United States Patent
Majeed et al.

(10) Patent No.: US 6,653,327 B2
(45) Date of Patent: Nov. 25, 2003

(54) CROSS-REGULIN COMPOSITION OF TUMERIC-DERIVED TETRAHYDROCURCUMINOIDS FOR SKIN LIGHTENING AND PROTECTION AGAINST UVB RAYS

(75) Inventors: Muhammed Majeed, Piscaraway, NJ (US); Vladimir Badmaev, Piscaraway, NJ (US)

(73) Assignee: Sabinsa Corporation, Piscataway, NJ (US)

( * ) Notice: Subject to any disclaimer, the term of this patent is extended or adjusted under 35 U.S.C. 154(b) by 0 days.

(21) Appl. No.: 09/972,150

(22) Filed: Oct. 9, 2001

(65) Prior Publication Data

US 2002/0197216 A1 Dec. 26, 2002

Related U.S. Application Data

(63) Continuation-in-part of application No. PCT/US00/08711, filed on Apr. 7, 2000.
(60) Provisional application No. 60/241,364, filed on Oct. 19, 2000, and provisional application No. 60/128,540, filed on Apr. 9, 1999.

(51) Int. Cl.$^7$ .................. A61K 31/445; A61K 7/42; A61K 7/00; A61K 31/28; A61K 31/30; A61K 31/075
(52) U.S. Cl. ................ 514/321; 424/59; 424/60; 424/195.1; 424/400; 424/401; 514/492; 514/499; 514/505; 514/720; 514/733
(58) Field of Search .................. 424/59, 60, 400, 424/401, 195.1; 514/321, 492, 499, 505, 720, 733

(56) References Cited

U.S. PATENT DOCUMENTS

| 5,266,344 A | 11/1993 | Mimura et al. ............. 426/546 |
| 5,861,415 A | * 1/1999 | Majeed et al. ............. 514/321 |

FOREIGN PATENT DOCUMENTS

| JP | 6-128133 | 5/1994 |
| WO | WO 95/18606 | 7/1995 |
| WO | WO 97/03674 | 2/1997 |
| WO | WO 99/55352 | 11/1999 |

OTHER PUBLICATIONS

Osawa, T. et al. "Antioxidative Activity of Tetrahydrocurcuminoids", Biosci. Biotech. Biochem. (1995); 59(9):1609–1612.
Venkateswarlu, S. et al. "Synthesis and Antibacterial Activity of Tetrahydrocurcuminoids", Asian Journal of Chemistry (2000); 12(1):141–144.
Osawa, T. et al. "Antioxidative Activity of Tetrahydrocurcumin", International Congress Series (1992), vol. 998, pp. 801–804.
Kobe Steel, "External Agent for Preventing UV Damage and Rough Skin–Contains Tetrahydro–curcumin Prepared by Reducing Curcumin Extracted from Turmeric Root", Derwent Publications Ltd., London, GB; AN 1994–188874; English Abstract of JP 06 128133.
Patent Abstracts of Japan, Publication No.: 06–128133, Published Oct. 5, 1994 and Derwent Abstract; WPI Acc. No.: 1994–188874/199423; for JP 6128133.
Walker, M.J. et al. "Curcumin in a Chemoprevention Model of Melanoma", Proceedings of the American Association for Cancer Research Annual Meeting (Mar. 1998) vol. 39, p. 19.
Ruby, A.J. et al. "Anti–tumor and antioxidant activity of natural curcuminoids", Cancer Letters (1995); 94:79–83.
Menon, L.A. et al. "Anti–metastatic activity of curcumin and catechin", Cancer Letters (1999); 141:159–165.
Menon, L.G. et al. "Inhibition of lung metastasis in mice induced by B16F10 melanoma cells by polyphenolic compounds", Cancer Letters (1995); 95:221–225.
Mulky, N. et al. "Antimutagenicity of Curcumins and Related Compounds: The Structural Requirement for the Antimutagenicity of Curcumins", Indian Drugs (1987); 25(3):91–95.
Nagabhushan, M. et al. "Curcumins as Inhibitors of Nitrosation in vitro", Mutation Research (1988); 202:163–169.
Sharma, O.P. "Antioxidant Activity of Curcumin and Related Compounds", Biochemical Pharmacology (1976); 25(15):1811–1812.

* cited by examiner

*Primary Examiner*—Shelle A. Dodson
(74) *Attorney, Agent, or Firm*—Arent Fox Kintner Plotkin & Kahn, PLLC

(57) ABSTRACT

The present invention is directed to a mixture of tetrahydrocurcuminoids which can be used for regulating random, intracellular protein cross-linking an optimizing cell electric potential in a patient.

15 Claims, No Drawings

CROSS-REGULIN COMPOSITION OF TUMERIC-DERIVED TETRAHYDROCURCUMINOIDS FOR SKIN LIGHTENING AND PROTECTION AGAINST UVB RAYS

CROSS-REFERENCE TO RELATED APPLICATIONS

This application is a continuation-in-part of pending U.S. Provisional Application 60/241,364 filed Oct. 19,2000, the subject matter of which is incorporated by reference herein in its entirety and this applications also is a continuation-in-part of pending PCT application U.S. 00/08711 filed Apr. 7,2000; which claims priority to U.S. Provisional Application No. 60/128,540 filed on Apr. 9, 1999 both of which are incorporated by reference herein in their entirety.

BACKGROUND OF THE INVENTION
Turmeric-Derived Phenolic Compounds in Skin Protection The role of curcuminoids, yellow phenolic compounds derived from turmeric roots (Curcuma longa, fam. Zingiberaceae), as topical antioxidants has been traditionally known in Asia and recently validated in laboratory experiments. Curcuminoids are reported to protect normal human keratinocytes from hypoxanthine/xanthine oxidase injury in in vitro studies, and they can protect the skin against a broad range of physical, chemical and biological factors injuring the skin[1]. Free radicals on the surface of the skin, generated through exposure to ultraviolet radiation, especially the UVB rays, chemicals or other environmental stress factors catalyze aging of the skin. Curcuminoids prevent free radical formation and scavenge free radicals in biological systems. This combined action was previously described as a Bio-protectant mechanism that protects the integrity of the living cell e.g. skin cell. The antioxidant effects of curcuminoids combined with their known inhibitory effects on cyclooxygenase 2 (Cox-2) render them useful as ingredients in anti-aging formulations and in topical formulations designed to maintain general skin health and integrity. Curcuminoids have also been found to inhibit the activity of tyrosinase, an enzyme that participates in melanogenesis, thereby preventing melanin formation with resultant lightening of the skin tone.[2]

Tetrahydrocurcuminoids (THC) are color-free compounds derived from curcuminoids, the yellow, parent compounds of THC, in the process of hydrogenation. The process of hydrogenation of curcuminoids can also occur naturally in the gastrointestinal tract.[3] The tetrahydrocurcuminoids' similar biological properties to curcuminoids combined with the lack of yellow color, render them useful in achromatic food and cosmetic applications that currently employ conventional synthetic antioxidants.

Like the curcuminoids, THC have also shown significant antioxidant action in a number of in vitro and preclinical studies. [4-9] THC are valued as the ultimate metabolites of the curcuminoids in vivo. Several independent studies validated the significant antioxidant effects of the tetrahydrocurcuminoids and protection of skin against free radicals and UVB rays.

DESCRIPTION OF THE INVENTION

Cross-Regulin Skin Protecting Mechanism

In the parent patent application of this application, Applicants have postulated the "cross-regulin" mechanism of THC. This mechanism has been described as both qualitatively and quantitatively different from the prior art. In the experimental work leading to the present application Applicant has evaluated THC in the in vivo model of skin injury by the chemical agent, TPA, and the physical agent, UVB rays. In addition, Applicants have tested the practical results of post-translational modification of proteins with the invention (i.e. its effect on enzyme tyrosinrase, the enzyme which participates in melanogenesis).

Effect of Cross-Regulin on TPA Induced Inflammation

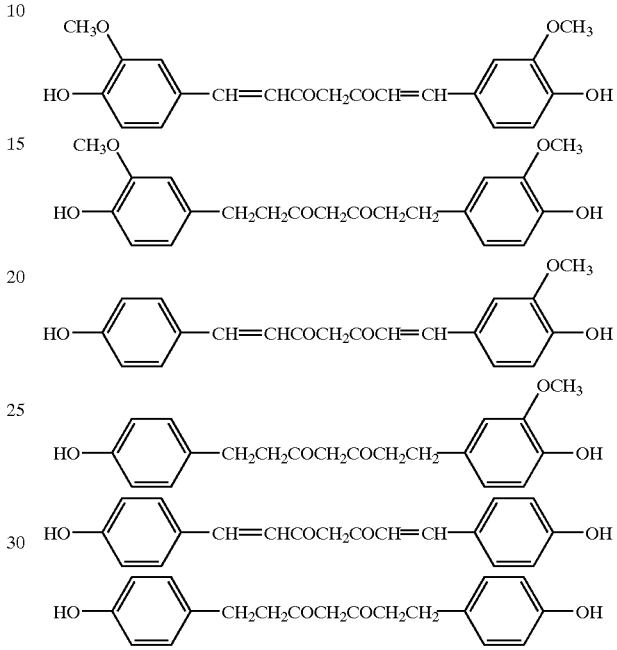

TPA induces many biochemical and morphological changes in mouse skin, which appear to be associated with inflammation and skin tumor promotion. For example, topical application of TPA to the skin of mice rapidly induced skin inflammation, increased epidermal ornithine decarboxylase activity, increased epidermal DNA synthesis, and increased the number of epidermal cell layers. Ornithine decarboxylase (ODC), the first enzyme in polyamine biosynthesis, is highly regulated by many trophic stimuli, and changes in its levels and organization correlate with cytoskeletal changes in human keratinocytes. Therefore, compounds which inhibit TPA and affect ODC synthesis will also affect the organization of the cytoskeleton and related events of post-translatational modification of proteins and crosslinking of proteins in the cytosol.

Prior art teaches that chemicals that inhibit TPA-induced biochemical and morphological changes usually inhibit TPA-induced tumor promotion in mouse skin. Applicants have postulated that the crossregulin composition of the invention is an optimal composition for protecting and preserving healthy living cells and for preventing cytoskeletons of the healthy living cells from being damaged by TPA and TPA-like tumor promoters. In an experiment conducted in vivo, the ear skin of Female CF-1 mice was treated with either 20 microliters acetone, TPA in acetone or TPA with Tetrahydrocurcuminoids of the invention [THC1], known Tetrahydrocurcuminoids [THC2] and known pure (synthetic) Tetrahydrocurcumin [THC3].

Five hours later the mice were sacrificed and ear punches were weighted (the higher the weight, score the more severe the inflammation of the treated ear-skin). Based on the weight score of the ear punches, the percent of inflammation inhibition was calculated. Protection against inflammation in decreasing order was furnished by THC1 of the invention, followed by THC2 of the prior art, and finally followed by THC3. The protective effect was dose-dependent concerning THC1 and THC2, while THC3 showed less protection at a dose of 0.36 mg compared to a dose of 0.12 mg. Prior art, as exemplified by the research data, cannot accomplish inhibition of the TPA induced ear edema above 80%. More than 80% inhibition of TPA-induced ear edema is necessary to prevent crosslinking of proteins which could trigger skin cancer. Therefore crossregulin action is not an inherent part of just any composition of THCs, but it is a specific composition that affords inhibition of the TPA mechanism by more than 80%.

Definition of Crossregulin's action:

Based on this experimental data, crossregulin's action is based on an anti-inflammatory and cancer preventive mechanism which is limited to any compound that inhibits the inflammatory process by at least 80% in two tested doses (i.e. 0.12 mg and 0.36 mg).

TABLE 1

Effects of THC on TPA-induced ear edema

| Treatment | No. mice | Wg/punch | % inhibition |
|---|---|---|---|
| 1. Acetone | 2 | 6.3 ± 0.1 | — |
| 2. TPA (1 nmol) | 5 | 14.2 ± 0.6 | — |
| 3. TPA THC1 0.12 | 4 | 7.7 ± 0.2 | 82.3 |
| 4. TPA THC1 0.36 mg | 4 | 7.2 ± 0.2 | 88.6 |
| 5. TPA THC2 0.12 mg | 4 | 9.6 ± 0.5 | 58.2 |
| 6. TPA THC2 0.36 mg | 4 | 8.3 ± 0.4 | 74.7 |
| 7. TPA THC3 0.12 mg | 4 | 7.8 ± 0.3 | 81.0 |
| 8. TPA THC3 0.36 mg | 4 | 8.1 ± 0.3 | 77.2 |

Female CF-1 mice were treated topically with 20 ul acetone, TPA (1 nmol) in acetone or TPA (1 nmol) and test compound in acetone on both ears. Five hours later the mice were sacrificed and ear punches were weighted. Data are expressed as the mean SE
THC1—invention, THC2—prior art Mimura, et at., U.S. Pat. No. 5,266,344 issued Nov. 30, 1993, THC3—Pure (synthetic) tetrahydrocurcumin.

Crossregulin Action of the Invention in Prevention of UVB Damage to the Skin

To further evaluate its crossregulin action, THC1 was tested against UVB-induced damage to the mouse epidermis. Exposure of unprotected skin to UVB causes sunburn, which in principle is an inflammatory reaction to thermal injury to the epidermis.

When a dose of UVB radiation, sufficient to induce erythema or thermal injury is administered to the healthy skin, this results in an increased number of epidermal cells with DNA strand breaks (terminal deoxynucleotidyl transferase-mediated dUTP nick end labeling-positive cells), a significant increase in numbers of thymine dimers formed within epidermal cells, and an increase in the number of epidermal cells with wild-type p53 and p21 proteins. These events start within 30 min after UVB exposure. DNA strand breaks increase maximally at 6 hr after UVB exposure, and the number of cells with DNA strand breaks or thymine dimers decrease markedly between 12 and 36 hours. The number of epidermal cells with wild-type p53 and p21 increases at 1 hour after UVB exposure and reaches maximum levels by 8 to 12 hours. The number of p53 and p21-positive cells decline markedly between 24 and 48 hours after UVB exposure.

Topical application of liposomes containing the DNA repairing enzyme, photolyase to UVB-irradiated skin and subsequent exposure to photoreactivating light decreased the number of UVB radiation-induced dimers by 40–45%. The UVB dose administered resulted in the suppression of the intercellular adhesion molecule-1 (ICAM-1), a molecule required for immunity and inflammatory events in the epidermis. In addition, in subjects hypersensitive to nickel sulfate, elicitation of the hypersensitivity reaction in irradiated skin areas was prevented. Photolyase-induced dimer repair completely prevented these UVB radiation-induced immunosuppressive effects as well as erythema and sunburn-cell formation. These studies demonstrate that topical application of photolyase is effective in dimer reversal and thereby leads to immunoprotection.

The potential UVB-protective effect of THC1 applied to the mouse skin was evaluated against untreated and unexposed skin as well as skin treated with the vehicle and dibenzoylmethane (DBM). DBM is a curcumin-related, beta-diketone analogue which has been reported to exhibit a significant inhibitory effect on 7,12-dimethylbenz[a]anthracene (DMBA)-induced mammary tumorigenesis in Sencar mice. The invention furnishes strong action in preventing sunburn and UVB light-induced formation of thymine dimers (Table 2, 3 and 4).

TABLE 2

Effect of topical application of THC of the invention on UVB light-induced formation of thymine dimers in mouse epidermis

| Treatment | No. mice | % thymine dimer cells | % protection |
|---|---|---|---|
| 1. No UVB | 3 | 0 | — |
| Acetone + UVB | 7 | 8.9 ± 0.02 | 0 |
| THC (10 umol) + UVB | 6 | 7.3 ± 0.03 | 24.7 |
| THC (20 umol) + UVB | 6 | 1.6 ± 1.30 | 82.0 |

Female SKH-1 mice(8–9 weeks old) were treated topically with 100 ul acetone or the test compound in 100 ul acetone. Five minutes later, the mice were irradiated with a single dose of UVB (30 mJ/cm2). The mice were killed one hour later, and skin samples were stored in a 10% formalin-phosphate buffer for thymine dimmers assay.

TABLE 3

Effect of Topical Application of Tetrahydrocurcumin on UVB light-induced Sunburn Lesions in SKH-1 Mice

| | | Days after last dose UVB | | | | |
|---|---|---|---|---|---|---|
| Treatment | No. mice | 3 | 4 | 5 | 6 | 7 |
| 1. )-)UVB | 8 | − | − | − | − | − |
| 2. Acetone (100 ul) | 8 | − | ++++ | +++ | +++ | ++ |
| 3. THC1 (10 uMol) | 8 | + | + | + | + | − |

Female SKH-1 mice (8–9 weeks old; 8 mice per group) were irradiated with UVB (180 mJ/cm2) once a day for 3 days. The mice were treated topically with vehicle or THC1 in vehicle once a day for 3 days at 10 min before UVB treatment. The 100 ul vehicle or THC1 treatments were continued once a day until the end of the experiment. The area of sunburn lesion (red color) were measured: (−) no sunburn; (+) slight sunburn; (++) sunburn; (+++) strong sunburn; (++++) very strong sunburn lesion.

TABLE 4

Effect of Dibenzoylmethane (DBM) and tetrahydrocurcuminoids (THC1) on UVB-induced Formation of Sunburn Cells and p21 Protein Levels in Epidermis of SKH-1 Mice

| Treatment | Percent Of Sunburn cells | Number of sunburn cells per 1 cm slide | Number of positive cells per 1 cm slide | % p21 |
|---|---|---|---|---|
| 1. -UVB | 0.1 | 1.8 ± 0.37 | 1.0 ± 0.63 | 0.04 |
| 2. Acetone + UVB (60 mJ/cm2) | 3.0 | 22.6 ± 2.79 | 38.0 ± 7.5 | 1.4 |
| 3. DBM (10 uM) + UVB | 1.2 | 13.2 ± 5.35 | 33.5 ± 7.49 | 1.2 |
| 4. DMB (20 um) + UVB | 0.9 | 8.6 ± 1.78 | 60.6 ± 12.9 | 2.2 |
| 5. THC1 (10 uM) + UVB | 1.6 | 17.8 ± 2.27 | 31.5 ± 8.66 | 1.0 |
| 6. THC1 (20 uM) + UVB | 1.4 | 10.6 ± 2.36 | 29.8 ± 5.12 | 1.1 |

Female Sencar mice (5 mice per group) were treated topically with 100 ul acetone or inhibitor in acetone at 5 min before a single dose of UVB (60 mJ/cm2) irradiation. The mice were killed 8 hours after UVB irradiation, and the skin biopsies were evaluated for sunburn cells and p21 protein.

THC1 has an UVB-protective effect comparable to DMB; however it may differ from DMB in the way it accomplishes that goal, and specifically in how it regulates Ras p21 protein (Ras p21 protein, an enzyme ubiquitous in the body cells, is central in the cell-signaling system). In cancer cells, this enzyme can undergo uncontrolled cross-linking which locks it in a cancer cell growth-promoting state. In view of the fact that UVB epidermal damage is associated with an increase in the number of p21 positive cells the sunburn-protective mechanism of THC1 (without increasing the p21 marker) is a favorable finding for the invention. In addition, the invention protects the epidermis against UVB exposure, resulting in significantly less sunburn which lasted one day less compared to the control group treated with vehicle (Table 3). Therefore the mechanism of the invention is unexpected and differs from prior art quantitatively and qualitatively. It is postulated that shortening the time of epidermal damage by the invention is due to stimulation of several defense compounds including photolyase and ICAM-1, which leads to epidermal DNA repair. It is further postulated that inhibition of tyrosinase, which furnishes a normalizing effect on photolyase, ICAM-1 and p21 protein is unique to the invention's crossregulin mechanism (i.e. post-translation modification of proteins).

Crossregulin Action of the Invention in Inhibition of Tyrosinase

As described in the patent applications, which have been incorporated herein, the invention modifies the activity of large group of enzymes called transglutaminases. Transglutaminases form a family of proteins that have evolved for specialized functions such as post-translational modification of proteins. In healthy tissues activation of transglutaminases is part of a protective cellular response that contributes to tissue homeostasis (e.g. blood clotting, replacement of old cells to give room for a new body cells). Crosslinking of proteins or its inhibition has been suggested as one of the mechanisms in post-translational modification of proteins. Among the various random or enzyme-mediated, crosslinking reactions, transglutaminase induced crosslinking activity has been proposed for its possible involvement in cell proliferation, differentiation and programmed death.

Transglutaminases exhibit true multifunctionality at the molecular level. The crosslinking activity can promote disparate biological phenomena depending on the state of health of the organism. For example, the oncogenes of certain types of skin moles undergo conversion to melanoma when UV rays trigger the crosslinking of ras proteins. In that case, inhibition of crosslinking will prevent initiation and progression of the malignancy.

On the other hand, activation of tissue transglutaminases in poorly differentiated melanoma may give rise to crosslinked protein which may result in apoptosis or cancerous cell death. In this example, crosslinking of proteins would have a positive impact on the clinical course of the neoplastic disease.

One of the important aspects of the invention is post-translational modification and inhibition of tyrosinase, an enzyme that is essential for synthesis of the skin pigment, melanin. The net effect of the invention is a significant inhibition of tyrosinase and melanin. However, comparison with prior art reveals that THC1 has least inhibitory effect on tyrosinase than either THC2 or THC3 (Table 5).

TABLE 5

Inhibitory concentrations (IC50) of THC on tyrosinase

| | IC50 (mcg/ml) |
|---|---|
| THC1 | 0.0493 |
| THC2 | 0.0155 |
| THC3 | 0.0000492 |

The assay for tyrosinase activity was based on the method of Sakuma et al (Arch Pharm Res. 1999. 22(4):335–339). 11

Epidermal melanin is known as a photoprotective agent which attenuates UV radiation.[12–14] Photoprotective action of melanin results in diminished erythema of skin exposed to UV rays. Melanin may play an important role in the absorption and scattering of UV light, which may be part of the mechanism in preventing skin cancer as well as an integral part of phototherapy in psoriasis.

In experimental animals, exposure to UVB radiation produces suppresses normal immune responses. Immune suppression is important in the development of nonmelanoma skin cancer, and it may influence the development and course of infectious skin diseases. It has been postulated that melanin can provide protection against immune suppression by UVB.

There is a consensus that high pigment content in skin is photoprotective against skin cancer, but induced pigment, as in tanning, may not be. The results of an in vitro study show that induced pigment is photoprotective and chemoprotective, but it is less effective in protection against mutagenesis by polychromatic UVB+UVA light.

The invention proposes a practical and safe solution to regulate functions of tyrosinase activity. Based on in vitro experimental data THC1 has considerable potential in inhibiting the process of melanogenesis, and this effect is explained by post-translational modification of tyrosinase by THC 1. The ability of the invention to inhibit melanogenesis is combined with its superior to the prior art ability to prevent the action of mutagenic compounds on skin cells and protect against sunburn. This combined mechanism of crossregulin is unique to a composition of this invention. This mechanism emphasizes the regulatory action of the invention rather than the inhibitory or stimulatory actions. A comparative study of the invention (THC 1) and prior art (THC2 and THC3) in the inhibition of tyrosinase has been conducted. In summary, the above experiments illustrate the unique, biological strength of THC1 in preventing TPA induced inflammation and carcinogenesis and inhibiting tyrosinase.

REFERENCES

1. Majeed, M. et al. (1995) Curcuminoids: Antioxidant Phytonutrients. Nutriscience Publishers, New Jersey.
2. Shirota et al. (1994) Tyrosinase inhibitors from crude drugs. Biol Pharm Bull 17(2):266–269
3. Pan, M. H. et al. (1999) Biotransformation of curcumin through reduction and glucuronidation in mice. Drug Metab. Dispos. 27(4):486–94.
4. Osawa, T. et al. (1995) Antioxidative activity of the tetrahydrocurcuminoids. Biosci. Biotechnol. Biochem. 59(9): 1609–12.
5. Sugiyama, Y. (1996) Involvement of the beta-diketone moiety in the antioxidative mechanism of Tetrahydrocurcumin. Biochem Pharmacol, 52(4):519–25 August 23
6. Nakamura, Y. et al. (1998) Inhibitory effects of curcumin and tetrahydrocurcuminoids on the tumor-promoter-induced reactive oxygen species generation in leukocytes, in vitro and in vivo. Jpn J Cancer Res, 89(4):361–70
7. Mukhopadhaya, A. et al. (1982). Anti-inflammatory and irritant activities of curcumin analogues in rats, Agents and Action. 12,2287.
8. Rao, T. S., et al. (1982) Anti-inflammatory activity of curcumin analogues. Ind J. Med.Res., 75 574–578
9. Bont'e, F. et al. (1997) Protective effects of curcuminoids on epidermal skin cells under free oxygen radical stress. Planta Med. 63(3):265–266.
10. Mimura, et al., U.S. Pat. No. 5,266,344 issued Nov. 30, 1993
11. Sakuma et al. (1999 August). Relationship between tyrosinase inhibitory action and oxidation-reduction potential of cosmetic whitening ingredients and phenol derivatives. Arch Pharm Res. 1999. 22(4):335–339).
12. Kollias N, Sayre R M, Zeise L, Chedekel M R. Photoprotection by melanin. J Photochem Photobiol B 1991 May;9(2): 135–160
13. Morison W L. Effects of ultraviolet radiation on the immune system in humans. Photochem Photobiol 1989 Oct;50(4):515–524.
14. Li W, Hill H Z. Induced melanin reduces mutations and cell killing in mouse melanoma. Photochem Photobiol 1997 Mar; 65(3):480–485.

What is claimed is:

1. A method for regulating random, intracellular protein cross-linking and optimizing cell electric potential in a patient in need of such regulation, comprising administering an effective amount of a mixture of tetrahydrocurcuminoids (THC) to the a patient in need of such regulation.

2. The method according to claim 1, wherein said random, intracellular cross-linking is a post-translational modification of a protein.

3. The method according to claim 1, wherein said random, intracellular cross-linking is modified by the THC to provide safe and effective mucosa, serosa or skin protection against physical, chemical and/or biologic elements.

4. The method according to claim 1, wherein said random, intracellular cross-linking is modified by the THC to provide safe and effective skin protection against UVA and/or and UVB.

5. The method according to claim 1, wherein said random, intracellular cross-linking is modified by the THC to effectively inhibit tyrosinase without causing side effects resulting from that inhibition.

6. The method according to claim 1, wherein said random, intracellular cross-linking is modified by the THC to regulate intracellular ras proteins.

7. The method according to claim 1, wherein said random, intracellular cross-linking is modified by the THC to inhibit protein cross-linking due to the presence of a malignancy.

8. The method according to claim 1, wherein said tetrahydrocurcuminoids comprise 70–80% tetrahydrocurcumin, 15–20% tetrahydrodemethoxycurcumin, and 2.5–6.5% tetrahydrobisdemethoxycurcumin.

9. A mixture comprising 70–80% tetrahydrocurcumin, 15–20% tetrahydrodemethoxycurcumin, and 2.5–6.5% tetrahydrobisdemethoxycurcumin, wherein said mixture is substantially colorless.

10. The method according to claim 1, wherein said mixture is in a form suitable for topical administration.

11. The method according to claim 1, wherein said mixture is in a form suitable for oral application.

12. The method according to claim 1, wherein said mixture is in a form suitable for parenteral application.

13. The mixture according to claim 9, wherein said mixture is in a form suitable for topical administration.

14. The mixture according to claim 9, wherein said mixture is in a form suitable for oral administration.

15. The mixture according to claim 9, wherein said mixture is in a form suitable for parenteral administration.

* * * * *

UNITED STATES PATENT AND TRADEMARK OFFICE
CERTIFICATE OF CORRECTION

PATENT NO.      : 6,653,327 B2
DATED           : November 25, 2003
INVENTOR(S)     : Majeed et al.

It is certified that error appears in the above-identified patent and that said Letters Patent is hereby corrected as shown below:

Title page,
Item [75], please amend the inventor's city of residence information as follows:
-- Muhammed Majeed, Piscataway, NJ (US); Vladimir Badmaev, Piscataway, NJ (US) --

Signed and Sealed this

Thirtieth Day of March, 2004

JON W. DUDAS
*Acting Director of the United States Patent and Trademark Office*